(12) United States Patent
Tiefensee et al.

(10) Patent No.: US 10,463,040 B2
(45) Date of Patent: Nov. 5, 2019

(54) COMPOSITION COMPRISING A PESTICIDE AND ISONONANOIC ACID N,N-DIMETHYL AMIDE

(71) Applicant: BASF SE, Ludwigshafen am Rhein (DE)

(72) Inventors: Kristin Tiefensee, Bad Duerkheim (DE); Ingo Fleute-Schlachter, Essen (DE); Verena Mormul, Mannheim (DE); Bernd Siegel, Otterstadt (DE)

(73) Assignee: BASF SE, Ludwigshafen am Rhein (DE)

( * ) Notice: Subject to any disclaimer, the term of this patent is extended or adjusted under 35 U.S.C. 154(b) by 15 days.

(21) Appl. No.: 15/560,817

(22) PCT Filed: Mar. 21, 2016

(86) PCT No.: PCT/EP2016/056078
§ 371 (c)(1),
(2) Date: Sep. 22, 2017

(87) PCT Pub. No.: WO2016/156075
PCT Pub. Date: Oct. 6, 2016

(65) Prior Publication Data
US 2018/0092352 A1 Apr. 5, 2018

(30) Foreign Application Priority Data
Mar. 31, 2015 (EP) .................................... 15162020

(51) Int. Cl.
*A01N 25/04* (2006.01)
*A01N 43/653* (2006.01)
*A01N 37/18* (2006.01)
*A01N 33/22* (2006.01)
*A01N 25/02* (2006.01)

(52) U.S. Cl.
CPC ............ *A01N 25/04* (2013.01); *A01N 25/02* (2013.01); *A01N 33/22* (2013.01); *A01N 37/18* (2013.01); *A01N 43/653* (2013.01); *A01N 2300/00* (2013.01)

(58) Field of Classification Search
CPC ...... A01N 25/04; A01N 33/22; A01N 43/653; A01N 37/18; A01N 2300/00; A01N 25/02
See application file for complete search history.

(56) References Cited

U.S. PATENT DOCUMENTS

| | | |
|---|---|---|
| 2,472,900 A | 6/1949 | Johnston et al. |
| 5,013,659 A | 5/1991 | Bedbrook |
| 5,559,024 A | 9/1996 | Leroux et al. |
| 6,222,100 B1 | 4/2001 | Anderson et al. |
| 2004/0059006 A1 | 3/2004 | Beilfuss et al. |
| 2008/0249193 A1 | 10/2008 | Frisch et al. |
| 2012/0157310 A1 | 6/2012 | Roechling et al. |
| 2014/0256716 A1 | 9/2014 | Baur et al. |

FOREIGN PATENT DOCUMENTS

| | | |
|---|---|---|
| DE | 19650107 A1 | 6/1998 |
| EP | 0039032 A2 | 11/1981 |
| EP | 0039032 A2 | 11/1981 |
| EP | 0044955 A1 | 2/1982 |
| EP | 0044955 A1 | 2/1982 |
| EP | 0242236 A1 | 10/1987 |
| EP | 0242246 A1 | 10/1987 |
| EP | 0257993 A2 | 3/1988 |
| EP | 0374753 A2 | 6/1990 |
| EP | 0392225 A2 | 10/1990 |
| EP | 0427529 A1 | 5/1991 |
| EP | 0451878 A1 | 10/1991 |
| EP | 494386 A1 | 7/1992 |
| EP | 0494386 A1 | 7/1992 |
| WO | 9200377 A1 | 1/1992 |
| WO | 9307278 A1 | 4/1993 |
| WO | 9534656 A1 | 12/1995 |
| WO | 9741218 A1 | 11/1997 |
| WO | 9802526 A1 | 1/1998 |
| WO | 9802527 A1 | 1/1998 |
| WO | 0026390 A2 | 5/2000 |
| WO | 0182685 A1 | 11/2001 |
| WO | 0215701 A2 | 2/2002 |

(Continued)

OTHER PUBLICATIONS

Moeller et al. (EP 0039032A2), 1981, Internet Translation, Patent Translate powered by EPO and Google from Espacenet, 3 pages.*
International Search Report and Written Opinion for International Application No. PCT/EP2016/056078, dated Apr. 25, 2016, 13 pages.
"Triethyl Citrate Handling/Processing", Technical Evaluation Report, Nov. 5, 2014, pp. 1-15.
Extended European Search Report for EP Patent Application No. 15162020.0, dated Jun. 3, 2015, 10 pages.
International Search Report and Written Opinion for PCT Patent Application No. PCT/EP2016/056078, dated Apr. 25, 2016, 15 pages.

*Primary Examiner* — John Pak
*Assistant Examiner* — Andriae M Holt
(74) *Attorney, Agent, or Firm* — Armstrong Teasdale LLP

(57) ABSTRACT

A composition comprising a pesticide and a certain carboxylic acid amide, i.e. isononanoic acid N,N-dimethyl amide, is described herein. Also disclosed is a method for controlling phytopathogenic fungi and/or undesirable plant growth and/or undesirable insect or mite infestation and/or for regulating the growth of plants, wherein the composition is allowed to act on the respective pests, the habitat thereof or the plants to be protected from the respective pest, on the soil and/or on undesirable plants and/or the crop plants and/or the habitat thereof. Furthermore, use of the carboxylic acid amide as a solvent for pesticides with no or low phytotoxicity is described.

8 Claims, No Drawings

(56) References Cited

FOREIGN PATENT DOCUMENTS

| WO | 03013225 A2 | 2/2003 |
|----|----|----|
| WO | 03014356 A1 | 2/2003 |
| WO | 03014357 A1 | 2/2003 |
| WO | 03018810 A2 | 3/2003 |
| WO | 03052073 A2 | 6/2003 |
| WO | 0416073 A2 | 2/2004 |
| WO | 2004106529 A2 | 12/2004 |
| WO | 2005020673 A1 | 3/2005 |
| WO | PCT-2005104844 | 11/2005 |
| WO | PCT-2006040022 | 4/2006 |
| WO | PCT-2013021045 | 2/2013 |

* cited by examiner

COMPOSITION COMPRISING A PESTICIDE AND ISONONANOIC ACID N,N-DIMETHYL AMIDE

CROSS-REFERENCE TO RELATED APPLICATIONS

This application is a U.S. National Phase Application of PCT/EP2016/056078, filed Mar. 21, 2016, which claims the benefit of priority to EP Application No. 15162020.0, filed Mar. 31, 2015, the contents of which are hereby expressly incorporated by reference in their entirety.

The present invention relates to a composition comprising a pesticide and a certain carboxylic acid amide, i.e. isononanoic acid N,N-dimethyl amide. The invention further relates to a method for controlling phytopathogenic fungi and/or undesirable plant growth and/or undesirable insect or mite infestation and/or for regulating the growth of plants, wherein the composition is allowed to act on the respective pests, the habitat thereof or the plants to be protected from the respective pest, on the soil and/or on undesirable plants and/or the crop plants and/or the habitat thereof. Furthermore, the invention relates to the use of the carboxylic acid amide as solvent for pesticides with no or low phytotoxicity.

The present invention comprises combinations of preferred features with other preferred features.

A large number of liquid concentrates are available to the agricultural markets, and each type of product has its advantages and disadvantages. For example, agrochemical pesticides have the advantages of containing a high concentration of active ingredients, and the ability to incorporate various ingredients into the composition to increase the efficacy of the composition. However, many agrochemicals, in particular pesticide technical grades, have a disadvantage in that they must be dissolved before use, which can be hazardous because of low flash points, environmental toxicity of the solvents, and require substantial mixing and long dissolving times.

There exists in the pesticide industry a great desire to find alternatives to currently used solvents such as isophorone, MBK, NMP, etc. which may be expensive, difficult to source and/or are environmentally unattractive due to their inherent phytotoxicity, toxicity e.g. teratogenicity or regulatory status.

Field tests have shown that certain environmentally favorable solvents may show a negative crop response with excess phytotoxicity.

Hence, there is a need in the agricultural industry for solvents that are capable of maintaining a wide variety of pesticides in solution and that have a reduced toxic response both to the environment and to the crop that is sprayed.

n-nonanoic acid is known in the art as super weed killer and as natural phytotoxic substances (see EP 494386 A1 and Gieben et al., Proceedings of the 4th ISOFAR Scientific Conference (2014)).

Amides and their use in agrochemical formulations as solvents for inhibiting crystal formation are generally known (e.g. EP 044955 A1).

However, the present inventors have found that the amide of nonanoic acid has a phytotoxic effect on the plants.

It was therefore an object of the present invention to identify a new carboxylic acid amide which is well suited to solve pesticides while being less phytotoxic to plants.

The object was solved by a composition comprising a pesticide and a carboxylic acid amide according to formula (I):

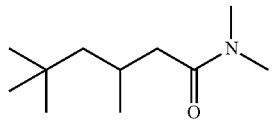

The present inventors have surprisingly found that this amide has no phytotoxic effect on plants while maintaining its property of solving a wide range of pesticides.

The term pesticide refers to at least one active substance selected from the group of the fungicides, insecticides, nematicides, herbicides, safeners, molluscicides, rodenticides and/or growth regulators. Preferred pesticides are fungicides, insecticides, herbicides and growth regulators. Especially preferred pesticides are herbicides, fungicides and insecticides. Mixtures of pesticides from two or more of the abovementioned classes may also be used. The skilled person is familiar with such pesticides, which can be found, for example, in Pesticide Manual, 14th Ed. (2006), The British Crop Protection Council, London. The above disclosed pesticides can be combined with the carboxylic acid amide of the present invention. Suitable pesticides that can be combined with the carboxylic acid amide of the present invention are:

A) strobilurins:
azoxystrobin, dimoxystrobin, coumoxystrobin, coumethoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, methyl 2-[2-(2,5-dimethylphenyloxymethyl)phenyl]-3-methoxyacrylate, 2-(2-(3-(2,6-dichlorophenyl)-1-methylallylideneaminooxymethyl)phenyl)-2-methoxyimino-N-methylacetamide;

B) carboxamides:
carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penflufen (N-(2-(1,3-dimethylbutyl)phenyl)-1,3-dimethyl-5-fluoro-1H-pyrazole-4-carboxamide), penthiopyrad, sedaxane, tecloftalam, thifluzamide, tiadinil, 2-amino-4-methyl-thiazole-5-carboxanilide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3,3-trimethylbutyl)phenyl)-1,3-dimethyl-5-fluoro-1H-pyrazole-4-carboxamide;

carboxylic acid morpholides: dimethomorph, flumorph, pyrimorph;

benzamides: flumetover, fluopicolide, fluopyram, zoxamid;

other carboxamides: carpropamid, diclocymet, mandipropamid, oxytetracyclin, silthiofam, N-(6-methoxypyridin-3-yl)cyclopropanecarboxamide;

C) azoles:
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole;

imidazoles: cyazofamid, imazalil, imazalil sulfate, pefurazoate, prochloraz, triflumizole;

benzimidazoles: benomyl, carbendazim, fuberidazole, thiabendazole;

others: ethaboxam, etridiazole, hymexazole, 2-(4-chlorophenyl)-N-[4-(3,4-dimethoxyphenyl)isoxazol-5-yl]-2-prop-2-ynyloxyacetamide;

D) nitrogenous heterocyclyl compounds pyridines: fluazinam, pyrifenox, 3-[5-(4-chlorophenyl)-2,3-dimethylisoxazolidin-3-yl]pyridine, 3-[5-(4-methylphenyl)-2,3-dimethylisoxazolidin-3-yl]pyridine;

pyrimidines: bupirimate, cyprodinil, diflumetorim, fenarimol, ferimzone, mepanipyrim, nitrapyrin, nuarimol, pyrimethanil;

piperazines: triforine;

pyrroles: fludioxonil, fenpiclonil;

morpholines: aldimorph, dodemorph, dodemorph acetate, fenpropimorph, tridemorph;

piperidines: fenpropidin;

dicarboximides: fluorimid, iprodione, procymidone, vinclozolin;

nonaromatic 5-membered heterocyclic rings: famoxadon, fenamidon, flutianil, octhilinone, probenazole, S-allyl 5-amino-2-isopropyl-3-oxo-4-orthotolyl-2,3-dihydropyrazole-1-thiocarboxylate;

others: acibenzolar-S-methyl, amisulbrom, anilazin, blasticidin-S, captafol, captan, quinomethionate, dazomet, debacarb, diclomezine, difenzoquat, difenzoquat methylsulfate, fenoxanil, folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxypyrimidin-2-yl)-2-methyl-1H-benzimidazole, 5-chloro-7-(4-methylpiperidin-1-yl)-6-(2,4,6-trifluorophenyl)-[1,2,4]triazolo[1,5-a]pyrimidine, 5-ethyl-6-octyl-[1,2,4]triazolo[1,5-a]pyrimidin-7-ylamine;

E) carbamates and dithiocarbamates thio- and dithiocarbamates: ferbam, mancozeb, maneb, metam, methasulphocarb, metiram, propineb, thiram, zineb, ziram;

carbamates: diethofencarb, benthiavalicarb, iprovalicarb, propamocarb, propamocarb hydrochloride, valiphenal, (4-fluorophenyl) N-(1-(1-(4-cyanophenyl)ethanesulfonyl)-but-2-yl)carbamate;

F) other fungicides guanidines: dodine, dodine free base, guazatine, guazatine acetate, iminoctadine, iminoctadine triacetate, iminoctadine tris(albesilate);

antibiotics: kasugamycin, kasugamycin hydrochloride hydrate, polyoxins, streptomycin, validamycin A;

nitrophenyl derivatives: binapacryl, dicloran, dinobuton, dinocap, nitrothal-isopropyl, tecnazene;

organometallic compounds: fentin salts such as, for example, fentin acetate, fentin chloride, fentin hydroxide;

sulfurous heterocyclyl compounds: dithianon, isoprothiolane;

organophosphorus compounds: edifenphos, fosetyl, fosetyl-aluminum, iprobenfos, phosphorous acid and its salts, pyrazophos, tolclofos-methyl;

organochlorine compounds: chlorthalonil, dichlofluanid, dichlorphen, flusulfamide, hexachlorobenzene, pencycuron, pentachlorophenol and its salts, phthalide, quintozene, thiophanate-methyl, tolylfluanid, N-(4-chloro-2-nitrophenyl)-N-ethyl-4-methylbenzenesulfonamide;

inorganic active substances: phosphorous acid and its salts, Bordeaux mixture, copper salts such as, for example, copper acetate, copper hydroxide, copper oxychloride, basic copper sulfate, sulfur;

biological products for controlling fungi, plant strengthening products: *Bacillus subtilis* strain NRRL No. B-21661 (for example the products RHAPSODY®, SERENADE® MAX and SERENADE® ASO from AgraQuest, Inc., USA), *Bacillus pumilus* strain NRRL No. B-30087 (for example SONATA® and BALLAD® Plus from AgraQuest, Inc., USA), *Ulocladium oudemansii* (for example BOTRY-ZEN from BotriZen Ltd., New Zealand), chitosan (for example AR-MOUR-ZEN from BotriZen Ltd., New Zealand).

others: biphenyl, bronopol, cyflufenamid, cymoxanil, diphenylamine, metrafenon, mildiomycin, oxine-copper, prohexadione-calcium, spiroxamin, tolylfluanid, N-(cyclopropylmethoxyimino-(6-difluoromethoxy-2,3-difluorophenyl)methyl)-2-phenylacetamide, N'-(4-(4-chloro-3-trifluoromethylphenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine, N'-(5-difluoromethyl-2-methyl-4-(3-trimethylsilanylpropoxy)phenyl)-N-ethyl-N-methylformamidine, N-methyl-(1,2,3,4-tetrahydronaphthalen-1-yl)-2-{1-[2-(5-methyl-3-trifluoromethylpyrazol-1-yl)acetyl]piperidin-4-yl}thiazole-4-carboxylate, N-methyl-(R)-1,2,3,4-tetrahydronaphthalen-1-yl 2-{1-[2-(5-methyl-3-trifluoromethylpyrazol-1-yl)acetyl]piperidin-4-yl}thiazole-4-carboxylate, 6-tert-butyl-8-fluoro-2,3-dimethylquinolin-4-ylacetate, 6-tert-butyl-8-fluoro-2,3-dimethylquinolin-4-yl methoxyacetate, N-methyl-2-{1-[2-(5-methyl-3-trifluoromethyl-1H-pyrazol-1-yl)acetyl]piperidin-4-yl}-N-[(1R)-1,2,3,4-tetrahydronaphthalen-1-yl]-4-thiazolecarboxamide;

G) growth regulators abscisic acid, amidochlor, ancymidole, 6-benzylaminopurine, brassinolide, butralin, chlormequat (chlormequat chloride), choline chloride, cyclanilid, daminozide, dikegulac, dimethipin, 2,6-dimethylpuridine, ethephon, flumetralin, flurprimidol, fluthiacet, forchlorfenuron, gibberellic acid, inabenfid, indole-3-acetic acid, maleic hydrazide, mefluidid, mepiquat (mepiquat chloride), metconazole, naphthaleneacetic acid, N-6-benzyladenine, paclobutrazole, prohexadione (prohexadione-calcium), prohydrojasmone, thidiazuron, triapenthenol, tributylphosphorotrithioate, 2,3,5-triiodobenzoic acid, trinexapac-ethyl and uniconazole;

H) herbicides acetamide: acetochlor, alachlor, butachlor, dimethachlor, dimethenamid, flufenacet, mefenacet, metolachlor, metazachlor, napropamid, naproanilid, pethoxamid, pretilachlor, propachlor, thenylchlor;

amino acid analogs: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

bipyridyls: diquat, paraquat;

carbamates and thiocarbamates: asulam, butylate, carbetamide, desmedipham, dimepiperat, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bromoxynil, dichlobenil, ioxynil;

imidazolinones: imazamethabenz, imazamox, imazapic, imazapyr, imazaquin, imazethapyr;

phenoxyacetic acids: clomeprop, 2,4-dichlorophenoxyacetic acid (2,4-D), 2,4-DB, dichlorprop, MCPA, MCPA-thioethyl, MCPB, mecoprop;

pyrazines: chloridazon, flufenpyr-ethyl, fluthiacet, norflurazon, pyridate;

pyridines: aminopyralid, clopyralid, diflufenican, dithiopyr, fluridone, fluroxypyr, picloram, picolinafen, thiazopyr;

sulfonylureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propylimidazo[1,2-b]pyridazin-3-yl)sulfonyl)-3-(4,6-dimethoxypyrimidin-2-yl)urea;

triazines: ametryne, atrazine, cyanazine, dimethametryne, ethiozine, hexazinone, metamitron, metribuzine, prometryne, simazine, terbuthylazine, terbutryne, triaziflam;

ureas: chlortoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, orthosulfamuron, penoxsulam, propoxycarbazone, pyribambenz-propyl, pyribenzoxim, pyriftalide, pyriminobac-methyl, pyrimisulfan, pyrithiobac, pyroxasulfon, pyroxsulam;

others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethlyl, chlorthal, cinmethylin, clomazone, cumyluron, cyprosulfamid, dicamba, difenzoquat, diflufenzopyr, *Drechslera monoceras*, endothal, ethofumesate, etobenzanid, fentrazamide, flumiclorac-pentyl, flumioxazin, flupoxam, fluorochloridon, flurtamon, indanofan, isoxaben, isoxaflutol, lenacil, propanil, propyzamide, quinclorac, quinmerac, mesotrione, methylarsenic acid, naptalam, oxadiargyl, oxadiazone, oxaziclomefon, pentoxazone, pinoxaden, pyraclonil, pyraflufen-ethyl, pyrasulfotol, pyrazoxyfen, pyrazolynate, quinoclamin, saflufenacil, sulcotrione, sulfentrazone, terbacil, tefuryltrione, termbotrione, thiencarbazone, topramezone, 4-hydroxy-3-[2-(2-methoxyethoxymethyl)-6-trifluoromethylpyridin-3-carbonyl]bicyclo[3.2.1]oct-3-en-2-one, ethyl (3-[2-chloro-4-fluoro-5-(3-methyl-2,6-dioxo-4-trifluoromethyl-3,6-dihydro-2H-pyrimidin-1-yl) phenoxy]pyridin-2-yloxy)acetate, methyl 6-amino-5-chloro-2-cyclopropylpyrimidine-4-carboxylate, 6-chloro-3-(2-cyclopropyl-6-methylphenoxy) pyridazin-4-ol, 4-amino-3-chloro-6-(4-chlorophenyl)-5-fluoropyridin-2-carboxylic acid, methyl 4-amino-3-chloro-6-(4-chloro-2-fluoro-3-methoxyphenyl)pyridin-2-carboxylate and methyl 4-amino-3-chloro-6-(4-chloro-3-dimethylamino-2-fluorophenyl)pyridin-2-carboxylate;

I) insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoat, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin, insect growth inhibitors: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazin; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramate;

nicotine receptor agonists/antagonists: clothianidin, dinotefuran, imidacloprid, thiamethoxam, nitenpyram, acetamiprid, thiacloprid, 1-(2-chlorothiazol-5-ylmethyl)-2-nitrimino-3,5-dimethyl-[1,3,5]triazinane;

GABA antagonists: endosulfan, ethiprole, fipronil, vaniliprole, pyrafluprole, pyriprole, N-5-amino-1-(2,6-dichloro-4-methylphenyl)-4-sulfinamoyl-1H-pyrazole-3-thiocarboxamide;

macrocyclic lactones: abamectin, emamectin, milbemectin, lepimectin, spinosad, spinetoram;

mitochondrial electron transport chain inhibitor (METI) I acaricides: fenazaquin, pyridaben, tebufenpyrad, tolfenpyrad, flufenerim;

METI II and III substances: acequinocyl, fluacyprim, hydramethylnone;

decouplers: chlorfenapyr;

inhibitors of oxidative phosphorylation: cyhexatin, diafenthiuron, fenbutatin oxide, propargite;

insect ecdysis inhibitors: cryomazin;

'mixed function oxidase' inhibitors: piperonyl butoxide;

sodium channel blockers: indoxacarb, metaflumizon;

others: benclothiaz, bifenazate, cartap, flonicamid, pyridalyl, pymetrozin, sulfur, thiocyclam, flubendiamid, chlorantraniliprole, cyazypyr (HGW86); cyenopyrafen, flupyrazofos, cyflumetofen, amidoflumet, imicyafos, bistrifluron and pyrifluquinazone.

The pesticide may comprise at least one water-insoluble pesticide. Water-insoluble pesticides may have a solubility in water of up to 10 g/l, preferably up to 1 g/l, and in particular up to 0.5 g/l, at 20° C.

The pesticide may be soluble in the carboxylic acid amide according to formula (I), e.g. in an amount of at least 5 g/l, preferably at least 20 g/l and in particular at least 40 g/l, at 20° C.

The pesticide may have a melting point of at least 40° C., preferably at least 60° C., and in particular at least 80° C.

In a preferred embodiment, the composition comprises a carboxylic acid amide according to formula (I) and a pesticide selected from the group consisting of anilide, nitrophenylether, pyridine, triazole, methoxycarbamate, strobilurine, pyrazole. In a further preferred embodiment, the composition comprises a carboxylic acid amide according to formula (I) and a pesticide selected from the group consisting of tebuconazole, pyraclostrobin and oxyfluorfen.

The compositions according to the invention can furthermore also comprise at least one emulsifier. Preferably, the at least one emulsifier is at least one non-ionic emulsifier. In a preferred embodiment, a single non-ionic emulsifier, preferably alkoxylated triglycerides, is added to the composition of the present invention and no further emulsifiers are added.

In another preferred embodiment, a combination of at least two non-ionic emulsifiers is added to the composition of the present invention.

The emulsifier may be any emulsifier conventionally used in agrochemical compositions and formulations.

In a preferred embodiment of the present invention, the at least one non-ionic emulsifier may be selected from alkoxylated triglycerides, preferably from ethoxylated triglycerides, more preferably from ethoxylated castor oils. Such ethoxylated castor oils may have an ethoxylation degree of from 10 to 60 EO units.

In a preferred embodiment, the at least one emulsifier may be at least one anionic emulsifier. The anionic emulsifier may be added as single anionic emulsifier or in combination with one or more other anionic emulsifier. The anionic emulsifier may be selected from the group consisting of aromatic alkylsulfonates Ca or Na salt and alkyl sulfosuccinate salt. Preferably, the aromatic alkylsulfonate is a $C_{12}$ benzene sulfonate, Ca salt, particularly preferably a linear $C_{12}$ benzene sulfonate, Ca salt. Preferably, the alkyl sulfosuccinate salt is a dialkyl sulfosuccinate salt, more preferably a $C_8$-$C_{10}$ branched or linear alkyl sulfosuccinate salt, even more preferably a branched $C_8$ sulfosuccinate salt, particularly preferably 2-ethylhexyl sulfosuccinate, Na salt. The anionic emulsifiers can be combined in a ratio of from 1:4 to 4:1.

In a further preferred embodiment, the at least one emulsifier is a combination of at least one non-ionic emulsifier and at least one anionic emulsifier. In this embodiment, the non-ionic emulsifier may be selected from the emulsifier described above or any emulsifier conventionally used in agrochemical compositions and formulations.

The compositions according to the invention can furthermore also comprise adjuvants conventionally used for agrochemical formulations, the choice of the adjuvants depending on the specific use form, the type of formulation or the active substance. Examples of suitable adjuvants are solvents, solid carriers, surface-active substances (such as surfactants, solubilizers, protective colloids, wetters and tackifiers), organic and inorganic thickeners, bactericides, antifreeze agents, antifoams, optionally colorants and adhesives (for example for the treatment of seed) or conventional adjuvants for bait formulations (for example attractants, feedants, bittering substances).

The compositions according to the present invention can also comprise further oil components and/or co-solvents other than carboxylic acid amide according to formula (I).

Suitable oil components and co-solvents are water or organic solvents such as mineral oil fractions of medium to high boiling point such as kerosene and diesel oil, furthermore coal tar oils and oils of vegetable or animal origin, aliphatic, cyclic and aromatic hydrocarbons, for example paraffins, tetrahydronaphthalene, alkylated naphthalenes and their derivatives, alkylated benzenes and their derivatives, alcohols such as methanol, ethanol, propanol, butanol and cyclohexanol, glycols, ketones such as cyclohexanone, gamma-butyrolactone, fatty acids and fatty acid esters, and polar solvents, for example amines such as N-methylpyrrolidone. In principle, it is also possible to use solvent mixtures and mixtures of the abovementioned solvents and water.

The compositions of the present invention can also comprise solid carriers. Solid carriers are mineral earths such as silicas, silica gels, silicates, talc, kaolin, limestone, lime, chalk, bole, loess, clay, dolomite, diatomaceous earth, calcium and magnesium sulfate, magnesium oxide, ground synthetic materials, fertilizers such as ammonium sulfate, ammonium phosphate, ammonium nitrate, ureas and vegetable products such as cereal meal, tree bark meal, wood meal and nutshell meal, cellulose powders or other solid carriers.

The compositions of the present invention can additionally comprise surface-active substances. Surface-active substances (adjuvants, wetters, tackifiers) which are suitable to be used in combination with the compositions of the present invention are the alkali metal, alkaline-earth metal, ammonium salts of aromatic sulfonic acids, for example of lignosulfonic acid (Borresperse® types, Borregaard, Norway), phenolsulfonic acid, naphthalenesulfonic acid (Morwet® types, Akzo Nobel, USA) and dibutylnaphthalenesulfonic acid (Nekal® types, BASF, Germany), and alkoxylates of fatty acids, alkyl ether, lauryl ether and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, polyoxyethylene or polyoxypropylene alkyl ethers, lauryl alcohol polyglycol ether acetate, sorbitol esters, lignin-sulfite liquors and proteins, denatured proteins, polysaccharides (for example methylcellulose), hydrophobe-modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone and their copolymers.

The composition according to the invention may comprise from 0.1 to 40% by weight, preferably from 1 to 30 and in particular from 2 to 20% by weight of surface-active substances (as disclosed above), the amount of the carboxylic acid amide not being taken into consideration.

Suitable thickeners that can be used in a composition of the present invention are compounds which impart to the formulation a modified flow behavior, i.e. high viscosity at rest and low viscosity in the agitated state. Examples are polysaccharides, proteins (such as casein or gelatins), synthetic polymers, or inorganic layered minerals. Such thickeners are commercially available, for example Xanthan Gum (Kelzan®, CP Kelco, USA), Rhodopol® 23 (Rhodia, France) or Veegum® (R. T. Vanderbilt, USA) or Attaclay®

(Engelhard Corp., N.J., USA). The thickener content in the formulation depends on the efficacy of the thickener. The skilled person will choose an amount suitable to obtain the desired viscosity of the formulation. The content will amount to from 0.01 to 10% by weight in most cases.

Bactericides may be added in order to stabilize the composition of the present invention. Examples of bactericides are those based on diclorophene and benzyl alcohol hemiformal and also isothiazolinone derivatives such as alkylisothiazolinones and benzoisothiazolinones (Acticide® MBS from Thor Chemie). Examples of suitable antifreeze agents are ethylene glycol, propylene glycol, urea and glycerol. Examples of antifoams are silicone emulsions (such as, for example, Silikon® SRE, Wacker, Germany or Rhodorsil®, Rhodia, France), long-chain alcohols, fatty acids, salts of fatty acids, organofluorine compounds and mixtures of these.

The composition according to the invention can preferably be present in the form of an agrochemical formulation. Examples of such formulations and their preparation are:

i) Water-soluble concentrates (SL, LS): 10 parts by weight of the active substances are dissolved using 90 parts by weight of water or a water-soluble solvent. Alternatively, wetters or other adjuvants are added. Upon dilution in water, the active substance dissolves. This gives a composition with an active substance content of 10% by weight.

ii) Dispersible concentrates (DC): 20 parts by weight of the active substances are dissolved in 70 parts by weight of NMP with addition of 10 parts by weight of a dispersant, for example polyvinylpyrrolidone. Upon dilution in water, a dispersion is obtained. The active substance content amounts to 20% by weight.

iii) Emulsifiable concentrates (EC): 15 parts by weight of the active substances are dissolved in 75 parts by weight of solvent naphta with addition of calcium dodecylbenzenesulfonate and castor oil ethoxylate (in each case 5 parts by weight). Upon dilution in water, an emulsion is obtained. The composition has an active substance content of 15% by weight.

iv) Emulsions (EW, EO, ES): 25 parts by weight of the active substances are dissolved in 35 parts by weight of xylene with addition of calcium dodecylbenzenesulfonate and castor oil ethoxylate (in each case 5 parts by weight). Using an emulsifier (for example Ultra-Turrax), this mixture is placed into 30 parts by weight of water and made into a homogeneous emulsion. Upon dilution in water, an emulsion is obtained. The composition has an active substance content of 25% by weight.

v) Suspensions (SC, OD, FS): 20 parts by weight of the active substances are comminuted with addition of 10 parts by weight of dispersants and wetters and 70 parts by weight of water or an organic solvent in a stirred-ball mill to give a finely divided active substance suspension. Upon dilution in water, a stable suspension of the active substance is obtained. The active substance content in the composition amounts to 20% by weight.

vi) Water-dispersible and water-soluble granules (WG, SG): 50 parts by weight of the active substances are ground finely with addition of 50 parts by weight of dispersants and wetters and formulated as water-dispersible or water-soluble granules by means of technical apparatuses (for example extrusion, spray tower, fluidized bed). Upon dilution in water, a stable dispersion or solution of the active substance is obtained. The composition has an active substance content of 50% by weight.

vii) Water-dispersible and water-soluble powders (WP, SP, SS, WS): 75 parts by weight of the active substances are ground in a rotor-stator mill with addition of 25 parts by weight of dispersants and wetters and also silica gel. Upon dilution in water, a stable dispersion or solution of the active substance is obtained. The active substance content of the composition amounts to 75% by weight.

viii) Gels (GF): in a ball mill, 20 parts by weight of the active substances, 10 parts by weight of dispersant, 1 part by weight of gelling agent and 70 parts by weight of water or an organic solvent are ground to give a fine suspension. Upon dilution with water, a stable suspension with an active substance content of 20% by weight is obtained.

ix) Dusts (DP, DS): 5 parts by weight of the active substances are ground finely and mixed intimately with 95 parts by weight of finely divided kaolin. This gives a dust with an active substance content of 5% by weight.

x) Granules (GR, FG, GG, MG): 0.5 part by weight of the active substances is ground finely and associated with 99.5 parts by weight of carriers. Conventional methods to this end are extrusion, spray-drying or the fluidized bed. This gives granules for direct application with an active substance content of 0.5% by weight.

xi) ULV solutions (UL): 10 parts by weight of the active substances are dissolved in 90 parts by weight of an organic solvent, for example xylene. This gives a composition to be applied directly with an active substance content of 10% by weight.

Stable in the context of the present invention means that no cream has formed within 24 hours after mixing components of a formulation. To measure the stability, 5% of the formulation (emulsion concentrate) is diluted in CIPAC water D in a 100 ml cylinder. The resulting oil-in-water emulsion is assessed after 1, 2, 4 and 24 hours. Perfectly stable are emulsions that do not form cream at all or have less than 0.5 ml cream.

In a preferred embodiment, the compositions of the present invention are emulsifiable concentrates (EC).

In general, the compositions of the present invention comprise from 0.01 to 95% by weight, preferably from 0.1 to 90% by weight, of the pesticides.

In most cases, the composition according to the invention comprises from 0.1 to 90% by weight of the carboxylic acid amide according to formula (I), preferably from 10 to 80% by weight and in particular from 20 to 70% by weight.

In a preferred embodiment, the composition according to the invention comprises 5 to 60% by weight of pesticide as defined above, 1 to 30% by weight of emulsifiers as defined above, 0 to 90% by weight of oil components and/or co-solvents, and 0.1 to 90% by weight of carboxylic acid amide according to formula (I), on the condition that the amounts add to 100% by weight.

In another preferred embodiment, the composition of the present invention further comprises water.

The user will generally use the composition according to the invention in a premetering device, in a knapsack sprayer, in a spray tank or in a spraying aircraft. Here, said composition is brought to the desired use concentration with water and/or buffer, optionally with addition of further auxiliaries, whereby the ready-to-use spray mixture (known as a tank mix) is obtained. Usually, 50 to 500 liters of the ready-to-use spray mixture are applied per hectare of utilizable agricultural area, preferably from 100 to 400 liters. In specific segments the amounts may also be above (e.g., fruit growing) or below (e.g., aircraft application) these amounts. The active substance concentrations in the ready-to-use preparations may be varied within substantial ranges. In general, they are between 0.0001 and 10%, preferably between 0.01 and 1%.

Oils of various types, wetters, drift reduction agents, stickers, spreaders, adjuvants, fertilizers, plant-strengthening products, trace elements, herbicides, bactericides, fungicides and/or pesticides may be added to the active substances or to the preparations comprising them, optionally also to the tank mix, immediately prior to use. These products can be admixed to the compositions according to the invention in the weight ratio 1:100 to 100:1, preferably 1:10 to 10:1. Adjuvants which are suitable within this context are in particular: organic-modified polysiloxanes, for example Break Thru S 240®; alcohol alkoxylates, for example Atplus® 245, Atplus® MBA 1303, Plurafac® LF 300 and Lutensol® ON 30; EO/PO block polymers, for example Pluronic® RPE 2035 and Genapol® B; alcohol ethoxylates, for example Lutensol® XP 80; and sodium dioctyl sulfosuccinate, for example Leophen® RA.

Depending on the nature of the desired effect, the application rates of the active substance when used in plant protection are between 0.001 and 2.0 kg of active substance per ha, preferably between 0.005 and 2 kg per ha, especially preferably between 0.05 and 0.9 kg per ha, in particular between 0.1 and 0.75 kg per ha.

The present invention furthermore relates to a method for controlling phytopathogenic fungi and/or undesirable plant growth and/or undesirable insect or mite infestation and/or for regulating the growth of plants, wherein the composition according to the present invention as defined above is allowed to act on the respective pests, the habit thereof or the plants to be protected from the respective pest, on the soil and/or on undesirable plants and/or the crop plants and/or the habitat thereof.

Examples of suitable crop plants are cereals, for example wheat, rye, barley, triticale, oats or rice; beet, for example sugar or fodder beet; pome fruit, stone fruit and soft fruit, for example apples, pears, plums, peaches, almonds, cherries, strawberries, raspberries, currants or gooseberries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capsicums; plants of the laurel family, for example avocados, cinnamon or camphor; energy crops and industrial feedstock crops, for example maize, soybeans, wheat, oilseed rape, sugar cane or oil palm; tobacco; nuts; coffee; tea; bananas; wine (dessert grapes and grapes for vinification); hops; grass, for example turf; sweetleaf (*Stevia rebaudania*); rubber plants and forest plants, for example flowers, shrubs, deciduous trees and coniferous trees, and propagation material, for example seeds, and harvested products of these plants.

The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding of polymers such as, for example, prenylated, acetylated or farnesylated residues or PEG residues.

Examples which may be mentioned are plants which, as the result of plant-breeding and recombinant measures, have acquired a tolerance for certain classes of herbicides, such as hydroxyphenylpyruvate dioxygenase (HPPD) inhibitors, acetolactate synthase (ALS) inhibitors such as, for example, sulfonylureas (EP-A 257 993, U.S. Pat. No. 5,013,659) or imidazolinones (for example U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073), enolpyruvylshikimate 3-phosphate synthase (EPSPS) inhibitors such as, for example, glyphosate (see, for example, WO 92/00377), glutamine synthetase (GS) inhibitors such as, for example, glufosinate (see, for example, EP-A 242 236, EP-A 242 246) or oxynil herbicides (see, for example, U.S. Pat. No. 5,559,024). For example, breeding and mutagenesis have given rise to Clearfield® oilseed rape (BASF SE, Germany), which features tolerance for imidazolinones, for example imazamox. With the aid of recombinant methods, crop plants such as soybeans, cotton, maize, beet and oilseed rape have been generated which are resistant to glyphosate or glufosinate, and these are available by the brand names RoundupReady® (glyphosate-resistant, Monsanto, U.S.A.) and Liberty Link® (glufosinate-resistant, Bayer CropScience, Germany).

Also comprised are plants which, with the aid of recombinant measures, produce one or more toxins, for example those from the bacterial strain *Bacillus*. Toxins which are produced by such genetically modified plants comprise, for example, insecticidal proteins of *Bacillus* spp., in particular from *B. thuringiensis*, such as the endotoxins Cry1Ab, Cry1Ac, Cry1F, Cry1Fa2, Cry2Ab, Cry3A, Cry3Bb1, Cry9c, Cry34Ab1 or Cry35Ab1; or vegetable insecticidal proteins (VIPs), for example VIP1, VIP2, VIP3, or VIP3A; insecticidal proteins from nematode-colonizing bacteria, for example *Photorhabdus* spp. or *Xenorhabdus* spp.; toxins from animal organisms, for example wasp, spider or scorpion toxins; fungal toxins, for example from Streptomycetes; plant lectins, for example from pea or barley; agglutinins; proteinase inhibitors, for example trypsin inhibitors, serine protease inhibitors, patatin, cystatin or papain inhibitors; ribosome-inactivating proteins (RIPs), for example ricin, maize RIP, abrin, luffin, saporin or bryodin; steroid-metabolizing enzymes, for example 3-hydroxysteroid oxidase, ecdysteroid IDP glycosyl transferase, cholesterol oxidase, ecdysone inhibitors or HMG CoA-reductase; ion channel blockers, for example inhibitors of sodium or calcium channels; juvenile hormone esterase; receptors for the diuretic hormone (helicokinin receptors); stilbene synthase, bibenzyl synthase, chitinases and glucanases. These toxins can also be produced, in the plants, in the form of pretoxins, hybrid proteins, truncated or otherwise modified proteins. Hybrid proteins are distinguished by a novel combination of different protein domains (see, for example, WO 2002/

015701). Further examples of such toxins or genetically modified plants which produce these toxins are disclosed in EP-A 374 753, WO 93/07278, WO 95/34656, EP-A 427 529, EP-A 451 878, WO 03/18810 and WO 03/52073. The methods for generating these genetically modified plants are known to the skilled person and explained, for example, in the abovementioned publications. A large number of the abovementioned toxins impart to the plants which produce them a tolerance for pests from all taxonomic classes of the arthropods, in particular beetles (Coeleropta), dipterans (Diptera) and lepidopterans (Lepidoptera) and nematodes (Nematoda). Genetically modified plants having one or more genes which code for insecticidal toxins are described for example in the abovementioned publications and are in some cases commercially available such as, for example, YieldGard® (maize varieties which produce the toxin Cry1Ab), YieldGard® Plus (maize varieties which produce the toxins Cry1Ab and Cry3Bb1), Starlink® (maize varieties which produce the toxin Cry9c), Herculex® RW (maize varieties which produce the toxins Cry34Ab1, Cry35Ab1 and the enzyme phosphinothricin N-acetyltransferase [PAT]); NuCOTN® 33B (cotton varieties which produce the toxin Cry1Ac), Bollgard® I (cotton varieties which produce the toxin Cry1Ac), Bollgard® II (cotton varieties which produce the toxins Cry1Ac and Cry2Ab2); VIPCOT® (cotton varieties which produce a VIP toxin); NewLeaf® (potato varieties which produce the toxin Cry3A); Bt-Xtra®, NatureGard®, KnockOut®, BiteGard®, Protecta®, Bt11 (for example Agrisure® CB) and Bt176 from Syngenta Seeds SAS, France, (maize varieties which produce the toxin Cry1Ab and the PAT enzyme), MIR604 from Syngenta Seeds SAS, France (maize varieties which produce a modified version of the toxin Cry3A, see in this context WO 03/018810), MON 863 from Monsanto Europe S.A., Belgium (maize varieties which produce the toxin Cry3Bb1), IPC 531 from Monsanto Europe S.A., Belgium (cotton varieties which produce a modified version of the toxin Cry1Ac) and 1507 from Pioneer Overseas Corporation, Belgium (maize varieties which produce the toxin Cry1F and the PAT enzyme).

Also comprised are plants which, with the aid of recombinant measures, produce one or more proteins which bring about an increased resistance to, or ability to withstand, bacterial, viral or fungal pathogens such as, for example, so-called pathogenesis-related proteins (PR proteins, see EP-A 0 392 225), resistance proteins (for example potato varieties which produce two resistance genes against *Phytophthora infestans* from the Mexican wild potato *Solanum bulbocastanum*) or T4 lysozyme (for example potato varieties which, as the result of the production of this protein, are resistant to bacteria such as *Erwinia amylvora*).

Also comprised are plants whose productivity has been improved with the aid of recombinant methods, for example by increasing the yield potential (for example biomass, grain yield, starch content, oil content or protein content), the tolerance for drought, salt or other limiting environmental factors, or the resistance to pests and fungal, bacterial and viral pathogens.

Also comprised are plants whose constituents, in particular for improving human or animal nutrition, have been modified with the aid of recombinant methods, for example by oil plants producing health-promoting long-chain omega-3-fatty acids or monounsaturated omega-9-fatty acids (for example Nexera® oilseed rape, DOW Agro Sciences, Canada).

The present invention also relates to the use of a carboxylic acid amide according to formula (I) as solvent for pesticides with no phytotoxicity.

No phytotoxicity in the context of the present invention means that in comparison to untreated plants, 0% of the treated plants have plant injury according to the phytotoxicity method described below.

Phytotoxicity in accordance with the present invention is determined by an assay where e.g. wheat (grasses) or black bindweed (broad leave), are treated with 2 g of a 1% Emulsion described below and are visually evaluated after 3 days of incubation. Plant injury covers the assessment of leave condition as well as resistance to lodging in case of grasses.

The emulsion is prepared by mixing 1% of concentrate with water. The concentrate consists of 7.5% of castor oil ethoxylate (30 EO), 2.5% Ca-Dodecylbenzolsulfonate and 90% carboxylic acid amide. The experimental period lasts for 3 days. During this time, the experimental plants receive optimum watering, with nutrients being supplied via the water used for watering.

The phytotoxicity is evaluated by awarding scores to the treated plants in comparison to untreated plants, i.e. treated with water only. The evaluation scale ranges from 0% to 100% phytotoxicity. The evaluation is done by visual examination. 0% phytotoxicity means that there are no differences between treated and untreated plants. Thus, no phytotoxicity in accordance with the present invention means that the treated plants do not have plant injury and there is no difference between treated and untreated plants.

Moderate phytotoxicity in accordance with the present invention means that only 1 to 10% of the treated plants have plant injury as compared to untreated plants. High phytotoxicity in accordance with the present invention means that >10 to 40% of the treated plants have plant injury as compared to untreated plants. Very high phytotoxicity in accordance with the present invention means that >40% of the treated plants have plant injury as compared to untreated plants.

The present invention also relates to a method for treating plants, thereby maintaining plant health comprising the step of mixing a carboxylic acid amide according to formula (I), with one or more pesticides described in the present disclosure, optionally the step of adding emulsifiers as defined above, oil components as described above and/or co-solvents as described above and optionally the step of adding the mixture to water.

The present invention also relates to a method for treating plants comprising the step of mixing a carboxylic acid amide according to formula (I), with one or more pesticides described in the present disclosure, optionally the step of adding emulsifiers as defined above, oil components as described above and/or co-solvents as described above and optionally the step of adding the mixture to water. Preferable, the carboxylic acid amide according to formula (I) in an amount of from 10% by weight to 90% by weight, preferably from 30% by weight to 80% by weight is mixed with one or more pesticides and optionally water.

Maintaining plant health in the context of the present invention means that crop does not suffer from undesired and uncontrolled side effects caused by the solvent like non-selective plant injuries when treated with the mixture above.

Finally, the present invention further relates to a method for producing the composition of the present invention comprising the step of mixing a carboxylic acid amide according to formula (I) with one or more pesticides described in the present disclosure, optionally the step of adding emulsifiers as defined above, oil components as described above and/or co-solvents as described above and optionally the step of adding the mixture to water.

Preferable, the carboxylic acid amide according to formula (I) in an amount of from 10% by weight to 90% by weight, preferably from 30% by weight to 80% by weight is mixed with one or more pesticides.

The preparation of carboxylic acid amides as defined above is generally known in the art, for example by reacting an amine with a carboxylic acid, an ester or an acid chloride as described for example in Mitchell, J A; Reid, E E, J. Am. Chem. Soc. 1931, 1879; U.S. Pat. No. 2,472,900; DE19650107; King, J F.; Rathore, R., J. Am. Chem. Soc. 1992, 3028.

The examples which follow illustrate the invention without imposing any limitation.

EXAMPLES

Example 1—Synthesis of Isononanoic Acid N,N-dimethyl Amide

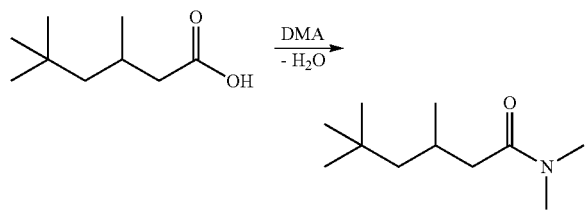

Procedure:

Isononanoic acid and sodium hypophosphite were added to a reactor heated to at least 175° C. under nitrogen atmosphere and reacted with dimethyl amine (DMA) for several hours. After cooling down to room temperature the raw product was distilled (vacuum distillation). The isononanoic acid N,N-dimethylamide was obtained as colorless or slightly yellow liquid with an overall yield of 86% (>98% GC).

Example 2—Phytotoxicity

Laboratory Test

Plants, i.e. wheat and black bindweed, were treated with 2 g of a 1% Emulsion described below and were visually evaluated after 3 days of incubation.

The emulsion was prepared by mixing 1% of concentrate with water. The concentrate consisted of 7.5% of castor oil ethoxylate (30 EO), 2.5% Ca-Dodecylbenzolsulfonate and 90% n-C9 N,N-dimethylamide or isononanoic acid N,N-dimethylamide.

Results are shown in Table 1.

TABLE 1

Phytotoxicty 3 days after treatment

| Carboxylic acid amide | Phytotoxicity |
|---|---|
| n-C9 N,N-dimethylamide[a] | +++ |
| Isononanoic acid N,N-dimethylamide | 0 |

[a]Comparative experiment, not inventive.
0 means no damage
+ means damage moderate
++ means damage high
+++ means damage very high

Example 3—Determination of the Max. Solubilitiy

The respective fungicide/herbicide was dissolved in the solvent of interest so that a supersaturated solution was obtained. The deposit was filtered off. The concentration of the fungicide/herbicide in the supernatant was determined via quantitative 1H-NMR spectroscopy.

TABLE 3

Solubility [%] of different fungicides/herbicide in carboxylic acid amide

| Carboxylic acid amide | Solubility [%] Tebuconazole | Solubility [%] Pyraclostrobin | Solubility [%] Oxyfluorfen |
|---|---|---|---|
| n-C9 N,N-dimethylamide[a] | 42 | 46 | 34 |
| Isononanoic acid N,N-dimethylamide | 35 | 40 | 31 |

[a]Comparative experiment, not inventive.

Example 4—Stable Emulsions

| Ingredients Actives | | Formulations [%] | | | |
|---|---|---|---|---|---|
| Tebuconazol | | 25 | 25 | 25 | 25 |
| Isononanoic acid N,N-dimethylamid | | 63 | 63 | | |
| n C9 N,N-dimethylamid | | | | 63 | 63 |
| Ca Dodecylbenzolsulfonat | | 2 | | 2 | |
| Castor oil ethoxylate (35 EO) | | 12 | 10 | 12 | 10 |
| Emulsion 5% in Cipac D 1 h | ml cream | stable | stable | stable | 3.0 |
| Emulsion 5% in Cipac D 2 h | ml cream | stable | stable | 2 | 8 |
| Emulsion 5% in Cipac D 4 h | ml cream | stable | stable | 3.0 | 8.0 |
| Emulsion 5% in Cipac D 24 h | ml cream | 0.5 | 0.5 | 3 | 8 |
| stable = no cream accepted level of cream = 2 ml cream max. after 24 h | | | | | |
| Oxyfluorfen | | 25 | 25 | 25 | 25 |
| Isononanoic acid N,N-dimethylamid | | 63 | 63 | | |
| n C9 N,N-dimethylamid | | | | 63 | 63 |
| Ca Dodecylbenzolsulfonat | | 2 | | 2 | |
| Castor oil ethoxylate (35 EO) | | 12 | 10 | 12 | 10 |
| Emulsion 5% in Cipac D 1 h | ml cream | stable | stable | 0.5 | 0.5 |
| Emulsion 5% in Cipac D 2 h | ml cream | stable | stable | 1 | 3 |
| Emulsion 5% in Cipac D 4 h | ml cream | stable | stable | 4.0 | 4.0 |
| Emulsion 5% in Cipac D 24 h | ml cream | stable | 0.5 | 6 | 6 |
| Cipac D: water hardness 432 ppm (Ca:Mg = 4:1) | | | | | |

The emulsion comprising the inventive amide was stable whereas the emulsion comprising n-C9 N,N-dimethylamide was unstable.

We claim:

1. A composition comprising one or more pesticides, at least one emulsifier, and a carboxylic acid amide according to formula (I),

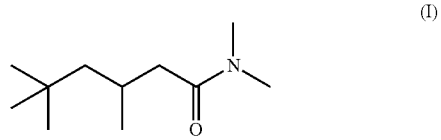

wherein the at least one emulsifier is a combination of at least one non-ionic emulsifier and at least one anionic emulsifier, and wherein the pesticide is selected from the group consisting of fungicides, herbicides, and insecticides.

2. The composition according to claim 1, wherein the composition comprises of from 0.1% by weight to 90% by weight of the carboxylic acid amide according to formula (I).

3. The composition according to claim 1, wherein the composition comprises
   5 to 60% by weight of pesticide,
   1 to 30% by weight of emulsifier,
   0 to 90% by weight of oil components and/or co-solvents, and
   0.1 to 90% by weight of carboxylic acid amide according to formula (I),
   on the condition that the amounts add to 100% by weight.

4. The composition according to claim 1, wherein the composition further comprises water.

5. A method for treating plants and/or for controlling phytopathogenic fungi and/or undesirable plant growth and/or undesirable insect or mite infestation and/or for regulating the growth of plants, wherein the composition as defined in claim 1 is allowed to act on a respective pest, a habitat thereof or plants to be protected from the respective pest, on soil and/or on undesirable plants and/or crop plants and/or a habitat thereof.

6. A method for producing the composition according to claim 1 comprising the step of mixing a carboxylic acid amide according to formula (I) as defined in claim 1 with one or more pesticides and at least one emulsifier,
   wherein the at least one emulsifier is a combination of at least one non-ionic emulsifier and at least one anionic emulsifier, and wherein the pesticide is selected from the group consisting of fungicides, herbicides, and insecticides.

7. The method for producing the composition according to claim 6 further comprising adding oil components and/or co-solvents.

8. The method for producing the composition according to claim 6, further comprising the step of adding the mixture to water.

* * * * *